(12) United States Patent
Dissanayake et al.

(10) Patent No.: US 11,501,457 B2
(45) Date of Patent: Nov. 15, 2022

(54) METHODS FOR IDENTIFYING DENDRITIC PORES

(71) Applicant: The Procter & Gamble Company, Cincinnati, OH (US)

(72) Inventors: Dissanayake Mudiyanselage Mahathma Bandara Dissanayake, Singapore (SG); Naoki Miyamoto, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 37 days.

(21) Appl. No.: 17/314,115

(22) Filed: May 7, 2021

(65) Prior Publication Data

US 2021/0350556 A1 Nov. 11, 2021

Related U.S. Application Data

(60) Provisional application No. 63/021,689, filed on May 8, 2020.

(51) Int. Cl.
*G06T 7/44* (2017.01)
*G06T 7/155* (2017.01)
*A61B 5/00* (2006.01)

(52) U.S. Cl.
CPC .............. *G06T 7/44* (2017.01); *A61B 5/0077* (2013.01); *A61B 5/442* (2013.01); *G06T 7/155* (2017.01); *G06T 2207/20056* (2013.01); *G06T 2207/30088* (2013.01)

(58) Field of Classification Search
CPC ......... G06T 2207/30088; G06T 7/0016; G06T 7/155; G06T 19/00; G06T 2207/20021; G06T 2207/30201; G06T 7/12; G06T 7/136; G06T 7/0012; G06T 2207/10024; G06T 7/44; G06T 2207/20056; G06T 2219/028; G06T 3/0068; G06T 2207/20152; G06T 2210/41; G06T 11/60; G06T 7/33; G06T 7/62; A61B 5/0077; A61B 5/442

See application file for complete search history.

(56) References Cited

U.S. PATENT DOCUMENTS

| 7,415,143 | B2 | 8/2008 | Grichnik |
| 7,531,184 | B2 | 5/2009 | Horino et al. |
| 7,799,319 | B2 | 9/2010 | Takeoka et al. |
| 8,094,186 | B2 | 1/2012 | Fukuoka et al. |

(Continued)

FOREIGN PATENT DOCUMENTS

| CN | 1961820 A | 5/2007 |
| CN | 105069818 A | 11/2015 |

(Continued)

OTHER PUBLICATIONS

Nonlinear Color Space and Spatiotemporal MRF for Hierarchical Segmentation of Face Features in Video—2013 (Year: 2013).*

(Continued)

*Primary Examiner* — Nizar N Sivji
(74) *Attorney, Agent, or Firm* — Alexandra S. Anoff

(57) ABSTRACT

A method for identifying a dendritic pore is provided. Line and pore images are obtained from a digital image of a subject's skin. These line and pore images are overlaid to identify those pores having at least one line intersecting the pore as dendritic pores.

14 Claims, 5 Drawing Sheets

(56) References Cited

U.S. PATENT DOCUMENTS

| | | | |
|---|---|---|---|
| 8,591,414 | B2 | 11/2013 | Kitamura et al. |
| 8,937,090 | B2 | 1/2015 | Kaminuma et al. |
| 10,812,719 | B2 | 10/2020 | Urakami |
| 2003/0086341 | A1 | 5/2003 | Wells et al. |
| 2003/0165429 | A1 | 9/2003 | Takeoka et al. |
| 2004/0218810 | A1 | 11/2004 | Momma |
| 2004/0264750 | A1 | 12/2004 | Znaiden et al. |
| 2005/0152930 | A1 | 7/2005 | Katsuta et al. |
| 2006/0034762 | A1 | 2/2006 | Takeoka et al. |
| 2007/0064985 | A1 | 3/2007 | Chhibber et al. |
| 2008/0212894 | A1* | 9/2008 | Demirli ............... G06T 11/00 382/276 |
| 2008/0269304 | A1 | 10/2008 | Katsuta et al. |
| 2009/0028380 | A1* | 1/2009 | Hillebrand ............ G06T 7/33 382/100 |
| 2009/0054744 | A1 | 2/2009 | Kitamura et al. |
| 2010/0084717 | A1 | 4/2010 | Tanaka |
| 2010/0158330 | A1 | 6/2010 | Lavi et al. |
| 2010/0309300 | A1 | 12/2010 | Chhibber et al. |
| 2011/0004019 | A1 | 1/2011 | Iida et al. |
| 2012/0008838 | A1 | 1/2012 | Guyon et al. |
| 2012/0053243 | A1 | 3/2012 | Kaminuma et al. |
| 2015/0086104 | A1* | 3/2015 | Miyamoto ............. C12Q 1/68 382/133 |
| 2015/0213619 | A1 | 7/2015 | Nakamura et al. |
| 2017/0206691 | A1* | 7/2017 | Harrises ............. G06T 11/60 |
| 2017/0270348 | A1 | 9/2017 | Morgana et al. |
| 2017/0270349 | A1 | 9/2017 | Polania Cabrera et al. |
| 2017/0270350 | A1 | 9/2017 | Maltz et al. |
| 2017/0270691 | A1 | 9/2017 | Maltz et al. |
| 2017/0272741 | A1 | 9/2017 | Maltz et al. |
| 2017/0372459 | A1 | 12/2017 | Tan et al. |
| 2019/0096093 | A1 | 3/2019 | Shinoda et al. |
| 2019/0244334 | A1* | 8/2019 | Arakawa ............... G06T 1/00 |
| 2019/0307231 | A1 | 10/2019 | Katsuyama |
| 2019/0325256 | A1 | 10/2019 | Van Bree et al. |
| 2020/0034990 | A1 | 1/2020 | Simpson et al. |
| 2020/0065998 | A1 | 2/2020 | Dissanayake et al. |

FOREIGN PATENT DOCUMENTS

| | | | | |
|---|---|---|---|---|
| CN | 107679507 | A | 2/2018 | |
| FR | 2954837 | A1 * | 7/2011 | ............. G06Q 30/06 |
| JP | H09175940 | A | 7/1997 | |
| JP | H09249526 | A | 9/1997 | |
| JP | H09327333 | A | 12/1997 | |
| JP | 2000321272 | A | 11/2000 | |
| JP | 2001190525 | A | 7/2001 | |
| JP | 2001278739 | A | 10/2001 | |
| JP | 2002154929 | A | 5/2002 | |
| JP | 2002265333 | A | 9/2002 | |
| JP | 2003146840 | A | 5/2003 | |
| JP | 2004002289 | A | 1/2004 | |
| JP | 2004364105 | A | 12/2004 | |
| JP | 2005097218 | A | 4/2005 | |
| JP | 2005281197 | A | 10/2005 | |
| JP | 2005345297 | A | 12/2005 | |
| JP | 2006056852 | A | 3/2006 | |
| JP | 2006188458 | A | 7/2006 | |
| JP | 2006305184 | A | 11/2006 | |
| JP | 2006327972 | A | 12/2006 | |
| JP | 2007012544 | A | 1/2007 | |
| JP | 2007055447 | A | 3/2007 | |
| JP | 2007077066 | A | 3/2007 | |
| JP | 2007099732 | A | 4/2007 | |
| JP | 2007204417 | A | 8/2007 | |
| JP | 2007302583 | A | 11/2007 | |
| JP | 2007310676 | A | 11/2007 | |
| JP | 2008019180 | A | 1/2008 | |
| JP | 2008037764 | A | 2/2008 | |
| JP | 4286724 | B2 | 4/2009 | |
| JP | 3150728 | U | 5/2009 | |
| JP | 2009120545 | A | 6/2009 | |
| JP | 2009215268 | A | 9/2009 | |
| JP | 2009242392 | A | 10/2009 | |
| JP | 2010007525 | A | 1/2010 | |
| JP | 2010047495 | A | 3/2010 | |
| JP | 2010047515 | A | 3/2010 | |
| JP | 2010077072 | A | 4/2010 | |
| JP | 2010143830 | A | 7/2010 | |
| JP | 2010260796 | A | 11/2010 | |
| JP | 2011127954 | A | 6/2011 | |
| JP | 2011161105 | A | 8/2011 | |
| JP | 2011184358 | A | 9/2011 | |
| JP | 2011209243 | A | 10/2011 | |
| JP | 2012021026 | A | 2/2012 | |
| JP | 2013196172 | A | 9/2013 | |
| JP | 2013216602 | A | 10/2013 | |
| JP | 2014062075 | A | 4/2014 | |
| JP | 2014120005 | A | 6/2014 | |
| KR | 100370271 | B1 | 1/2003 | |
| KR | 100777057 | B1 | 11/2007 | |
| TW | 201513892 | A | 4/2015 | |
| WO | 2005070372 | A1 | 8/2005 | |
| WO | 207111344 | A1 | 10/2007 | |
| WO | 2009084156 | A1 | 7/2009 | |
| WO | 2012014417 | A1 | 2/2012 | |
| WO | 2012017734 | A1 | 2/2012 | |
| WO | 2012121309 | A1 | 9/2012 | |
| WO | 2015045167 | A1 | 4/2015 | |

OTHER PUBLICATIONS

Based on machine learning for personalized skin care products recommendation engine—2020 (Year: 2020).*

AA01306 PCT Search Report and Written Opinion for PCT/US2019/046255 dated Jan. 13, 2020.

All Office Actions, U.S. Appl. No. 16/546,837.

Belattar, et al., "Similarity Measures for Content-Based Dermoscopic Image Retrieval: A Comparative Study", In Proceedings of the First International Conference on New Technologies of Information and Communication, Nov. 8, 2015, 6 Pages.

Taeg Sang Cho, et al., "A Reliable Skin Mole Localization Scheme", In Proceedings of the IEEE 11th International Conference on Computer Vision, Oct. 14, 2007, 8 Pages.

Tan, et al., "An Intelligent Decision Support System for Skin Cancer Detection from Dermoscopic Images", In Proceedings of the 12th International Conference on Natural Computation, Fuzzy Systems and Knowledge Discovery, Aug. 13, 2016, pp. 2194-2199.

Zhang, et al., "Skin Pores Detection for Image-Based Skin Analysis", In proceedings of the International Conference on Intelligent Data Engineering and Automated Learning, Nov. 2, 2008, pp. 233-240.

PCT Search Report and Written Opinion for PCT/US2021/031206 dated Aug. 13, 2021, 14 pages.

Chin Chiun-Li et al: 11 Skin condition 1-16 detection of smart phone face image using multi-feature decision method Nov. 8, 2017 pp. 379-382.

* cited by examiner

METHODS FOR IDENTIFYING DENDRITIC PORES

FIELD OF THE INVENTION

The present invention relates generally to methods for identifying dendritic pores on skin.

BACKGROUND OF THE INVENTION

Skin features, such as pores and lines, are common concerns in cosmetic dermatology and non-medical cosmetic industries. Presence of enlarged skin pores, for example, may negatively impact skin elasticity which would then lead to skin sagging especially around the nose and cheek areas of the face of an individual. This has led many individuals, especially younger individuals, seeking various treatment options to help address issues related to skin pores. Fine lines and wrinkles are classic symptoms of aging skin but are particularly challenging to identify in younger individuals. There is an opportunity to better identify skin features of aging skin in younger individuals so preventive treatment measures can be taken to prevent or delay age-related symptoms from developing, and efficacy between any two cosmetic treatments can be better assessed. Non-invasive methods are typically used to evaluate skin features, such as a dermascope or confocal laser microscope. However, a limitation of such methods is that only a very small or narrow area (for example, 15 mm in diameter) can be examined at each measurement. As such, it may not be suitable for measuring a larger area such as the entire cheek area or the entire face area as multiple measurements would have to be taken. Moreover, these approaches are not readily accessible to many users and require some degree of training to operate. There is an on-going opportunity to better develop more accurate and/or precise methods to identify skin features, that are user friendly, so that optimized non-medical cosmetic skin care treatment regimens can be recommended and/or developed for individuals, particularly younger individuals who generally have less pronounced skin features comparted to older individuals.

SUMMARY OF THE INVENTION

The invention is based, at least in part, on the discovery of a dendritic pore, and further the role dendritic pores in assessing skin and consequently the skin care needs of an individual. The methods can also be applied to help in the development of skin care treatment approaches. A dendritic pore is a pore where a line or wrinkle intersects the pore. One aspect of the invention provides for a method of identifying a dendritic pore comprising the steps: obtaining a digital image of a subject's skin; generating a line image having lines from the obtained digital image; generating a pore image having pores from the obtained digital image; overlaying the line image and the pore image in a first overlay image to identify those pores having at least one line intersecting the pore thereby identifying the dendritic pore.

An advantage is the increased sensitivity of methods for assessing skin features compared to other methods, particularly in younger aged subjects.

BRIEF DESCRIPTION OF THE DRAWINGS

The present invention will now be described, by way of illustrative example only, with reference to the accompanying drawings, of which.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope of the present invention is not intended to be limited to the particular forms disclosed and the invention covers all modifications, equivalents, and alternatives falling within the spirit and scope of the invention as defined by the claims.

As used herein, the term "cosmetic" means a non-medical method of providing a desired visual effect on an area of the human body. The visual cosmetic effect may be temporary, semi-permanent, or permanent.

As used herein, the term "facial area" refers to a user's entire face or a portion of a user's face, including, but not limited to one or more of the following areas: cheek, nose, forehead, mouth, chin, periorbital area and neck area.

As used herein, the term "image capturing device" refers to a device, system or instrument that can capture and/or record images (e.g., still pictures or videos), preferably digital images. The device may be part of a clinical imaging system or a beauty counter skin evaluation system. The device may be part of a mobile device or a smart device, which includes a mobile phone, a smart phone, a tablet, a laptop, a watch, a personal digital assistant, or may be part of a personal computer, or may be a standalone camera such as a handheld camera. The device may also include a built-in light source (e.g., a flash) for emitting light.

As used herein, the term "skin" refers to the outermost protective covering of mammals that is composed of cells such as keratinocytes, fibroblasts and melanocytes. Skin includes an outer epidermal layer and an underlying dermal layer. Preferably the skin is facial area skin.

As used herein, the term "skin feature" refers to a feature on the skin of a subject, including, but not limited to one or more of the following: pore, shine, line (including wrinkles), spot, hair, mole, pimple acne, blackhead, whitehead, and any combinations thereof.

As used herein, the term "subject" refers to a person upon whom the use of methods (and systems) described herein.

Figure 1:
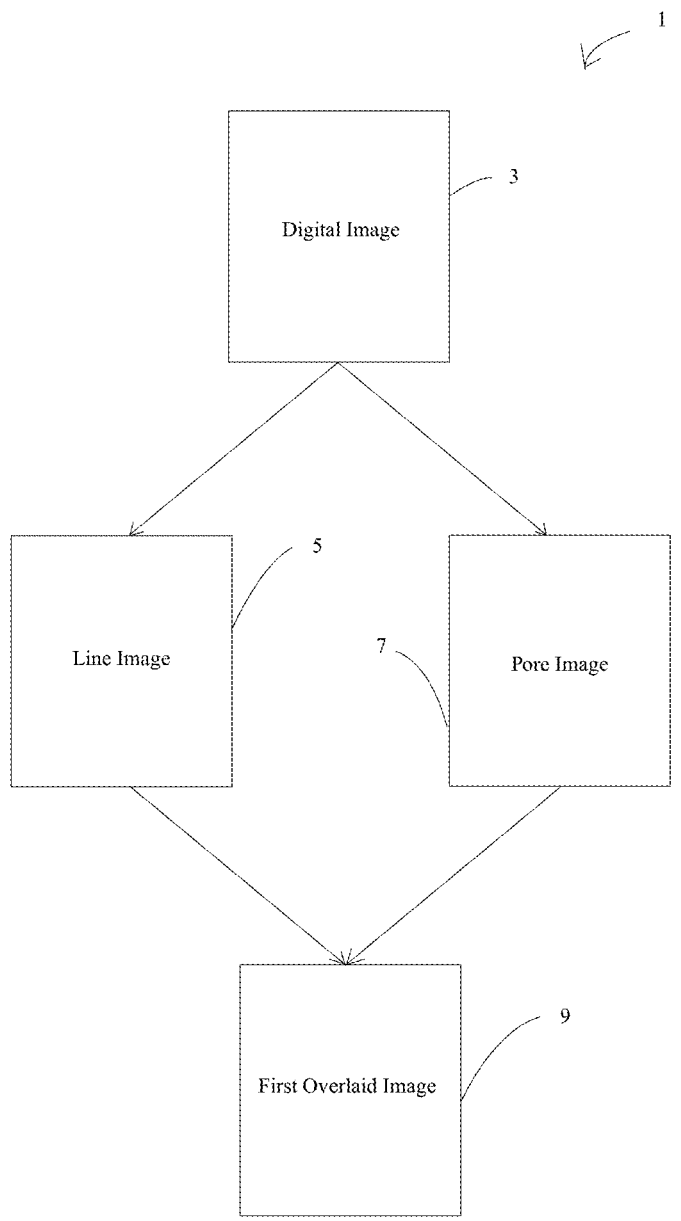
FIG. 1 depicts a general flow diagram of a method for identifying a dendritic skin pore.

FIG. 1 is a general flow diagram of a method of identifying a dendritic pore (1) is provided. A first step is obtaining a digital image of the subject (3). From this digital image, a line image (5) is generated (5). Also, from this digital image (3) a pore image (7) is generated. Lastly, the line image (5) and the pore image (7) are overlaid with each other to provide a first overlay image (9) to identify those pores having at least one line intersecting the pore thereby identifying the dendritic pore.

Figure 2:
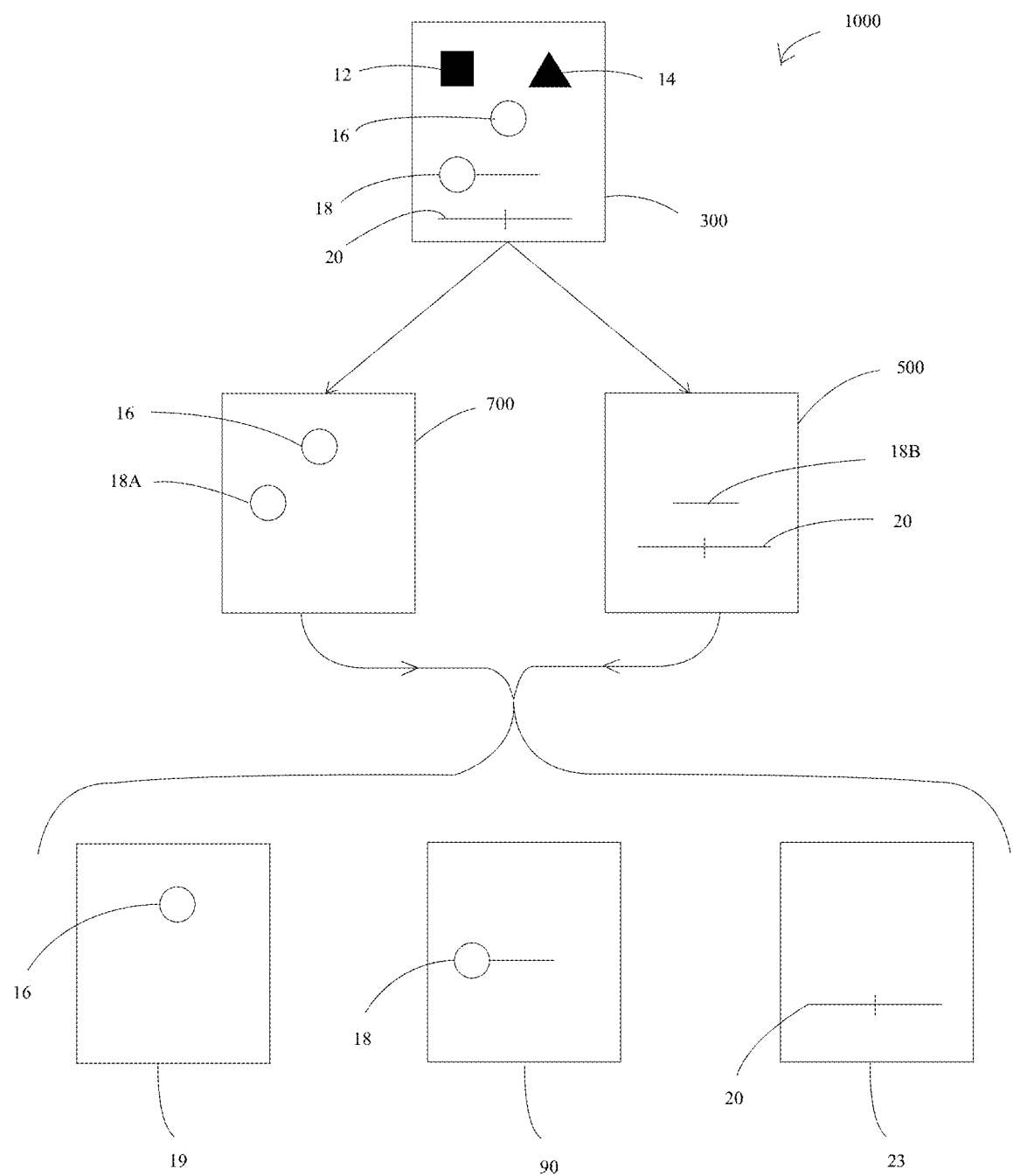
FIG. 2 depicts a more detailed version of the method depicted in FIG. 1.

FIG. 2 is a more detailed flow diagram of FIG. 1 (1000). Similarly, the method (31) provides a digital image of the subject (300). The image may be obtained from an image capturing device. For example, the image capturing device is an imaging system that uses Canon® 5D Mark II full frame Digital Single Lens Reflex (DSLR) camera with custom light settings and polarization filters, such as Visia®-CR imaging system (Canfield Scientific, New Jersey, USA), which comprises a Canon® 5D Mark II DSLR camera. If the image is an image of an entire face or other large areas of the human body, and the region of interest pertains to only a portion of such an image. Alternatively, the image may be retrieved from computer memory (wherein the stored image is captured from an earlier point in time by the image capturing device).

The digital image of the subject (300) may show a plurality of skin features. These skin features may include, for example, spots (12) and moles (14) and the like. Notably, the skin features also include independent pores (16), lines (20), and dendritic pores (18). Some of these skin features are not be visible to the unaided eye. It is appreciated that not all these skin features are readily apparent in the digital image of the subject (300) without the digital processing steps subsequently described.

Dendritic pores (18) are those pores connected with at least one line. A dendritic pore is a pore where a line intersects the pore. For example, an intersecting line can be one that either touches an outer boundary of the pore or one that passes through the pore. A dendritic pore may be intersected by to 2, 3, 4, or more lines. One dendritic pore may be connected to other dendritic pores (via shared lines (or wrinkles)). In turn, these interconnected dendritic pores may form clusters (wherein clusters may be separated from each other). Without wishing to be bound by theory, dendritic pores are correlated with chronological aging. Dendritic pores can develop over time, in the facial area, by physically loaded stress due to frequent motion of facial expressions, and/or decreased elasticity due to aging. This correlation is demonstrated in Example 1. That is, there is an increase in the average number of dendritic pores in a defined unit area as the age of subject increases. It is important to study dendritic pores in cosmetic research as a phenotype of skin health and aging. Furthermore, without wishing to be bound by theory, the segmentation of dendritic pores (18) from independent pores (16) (i.e., pores that are not intersected by any lines) could be important in communicating to young users (e.g., 18 to 25 years of age) premature signs of skin aging and its perception. The methods herein may help enable the development of innovative new cosmetic skin care products or regimens, and skin cosmetic diagnosis.

Still referencing FIG. 2, from the digital image of the subject (300), a pore image (700) is generated. A pore image (700) is generated by extracting the pores (16, 18A) from the digital image of the subject (300). These pores can come from an independent pore (16) or dendritic pores (18A). There is a dendritic pore (18A) is in the generated pore image (700) but without the intersecting line (18B). Although not shown, in a preferred example, the extracted pore image (700) identifies a boundary of each of the pores (16, 18A, 18B). The pore image (700) may be extracted by segmenting the digital image of the subject (300). Segmentation the digital image of the subject (300) may be performed by one or more methods, such as a thresholding method, color-based segmentation method, transform method, texture method, or combinations thereof. Preferably, segmentation of digital image of the subject (300) is performed by a thresholding method, and more preferably performed by an adaptive thresholding method.

Similarly, from the digital image of the subject (300), a line image (500) is generated. A line image (500) is generated be extracting lines (18B, 20) from the digital image of the subject (300). The lines can come from an independent line (20) (i.e., not intersecting a pore) or a line associated with one or more dendritic pores (18B) by intersecting the pore. Although not shown, in a preferred example, the extracted line image (500) identifies a boundary of each of the lines (18B, 20). The line image (500) may be extracted by segmenting the digital image of the subject (300). Segmentation can be according to the methods previously described.

Optionally, to increase the accuracy of identifying the boundary of each of the pores (16, 18A) and/or the lines (18B, 20) the digital image of the subject (300) may be processed prior to extracting the pore image (700) and/or the line image (500). For example, histogram equalization may be performed to the digital image of the subject (300) for enhancing contrast and/or improving illumination of the image (300) to obtain a histogram-equalized image. The histogram-equalized image or the unprocessed image (300) may be filtered to remove one or more skin features (e.g., spots (12) and moles (14)) as desired to obtain a filtered image. Filters such as a frequency filter may be used to filter the histogram-equalized image or the unfiltered image (300). Examples of frequency filters include a Fast Fourier Transformation filter used with a Band Pass filter, and a Difference of Gaussian filter. Preferably, a Difference of Gaussian filter is used to filter the histogram-equalized image of the image (300). After the histogram-equalized image or the filtered image is obtained, segmentation is performed on the histogram-equalized image or the filtered image to extract the pore image (700) and/or line image (500).

Optionally, one or more additional filters may be used to further increase the accuracy of identifying the boundary of each of the skin pores (16, 18A) and/or lines (18B, 20). For example, watershed transformation filter may be used to divide skin pores (16, 18A) which are connected which otherwise may be identified as a boundary line (not shown). By analogy the same watershed filter may be used to divide lines (18B, 20). Another example of a filter is a shape filter. The shape filter may comprise defining the pore by pore geometry parameters; preferably wherein the pore geometry parameters are pore area (preferably $25{,}000\text{-}1 \times 10^6$ micron$^2$), diameter (preferably 175-1100 microns), width/length aspect ratio (preferably 0.3-1) and combination thereof.

The shape filter comprises defining the lines by line geometry parameters; preferably wherein the line geometry parameters are selected from line thickness (preferably wherein the line thickness is greater than 35 microns, more preferably from 40 microns to 1 cm) line length (preferably greater than 200 microns, more preferably from 250 microns to less than 5 cm, preferable less than 3 cm, more preferably from 250 microns to 1 cm), and combinations thereof.

Although not shown, preferably the digital image of the subject is processed (according to one more of the aforementioned steps). More preferably, a line image and a pore image are generated from the processed image. Yet further a binary line image and/or binary pore image is generated. Optionally, but preferably, an intersection step can be applied to pore and/or line binary images to help identify very small pores detected as lines in the line binary image.

A unionization step will help identify both lines and pores in the binary line and/or pore binary images, respectively. Image processing programs and programming languages for example MATLAB®, Python™, OpenCV, Java™, ImageJ can be used to implement above steps.

Lastly, and still referencing FIG. 2, the line image (5) and pore image (7) are overlaid with each other to identify those pores having at least one line intersecting a pore thereby identifying the dendritic pore(s) (18) in the first overlaid image. A second overlaid image (19) provides independent pores (16). A third overlaid image (23) will provides independent lines (20). Preferably morphological reconstruction is applied to the first overlay image to identifying those pores having at least one line intersecting the pore. In one non-limiting example, MATLAB® is used for the implementation of morphological reconstruction.

Figure 3:
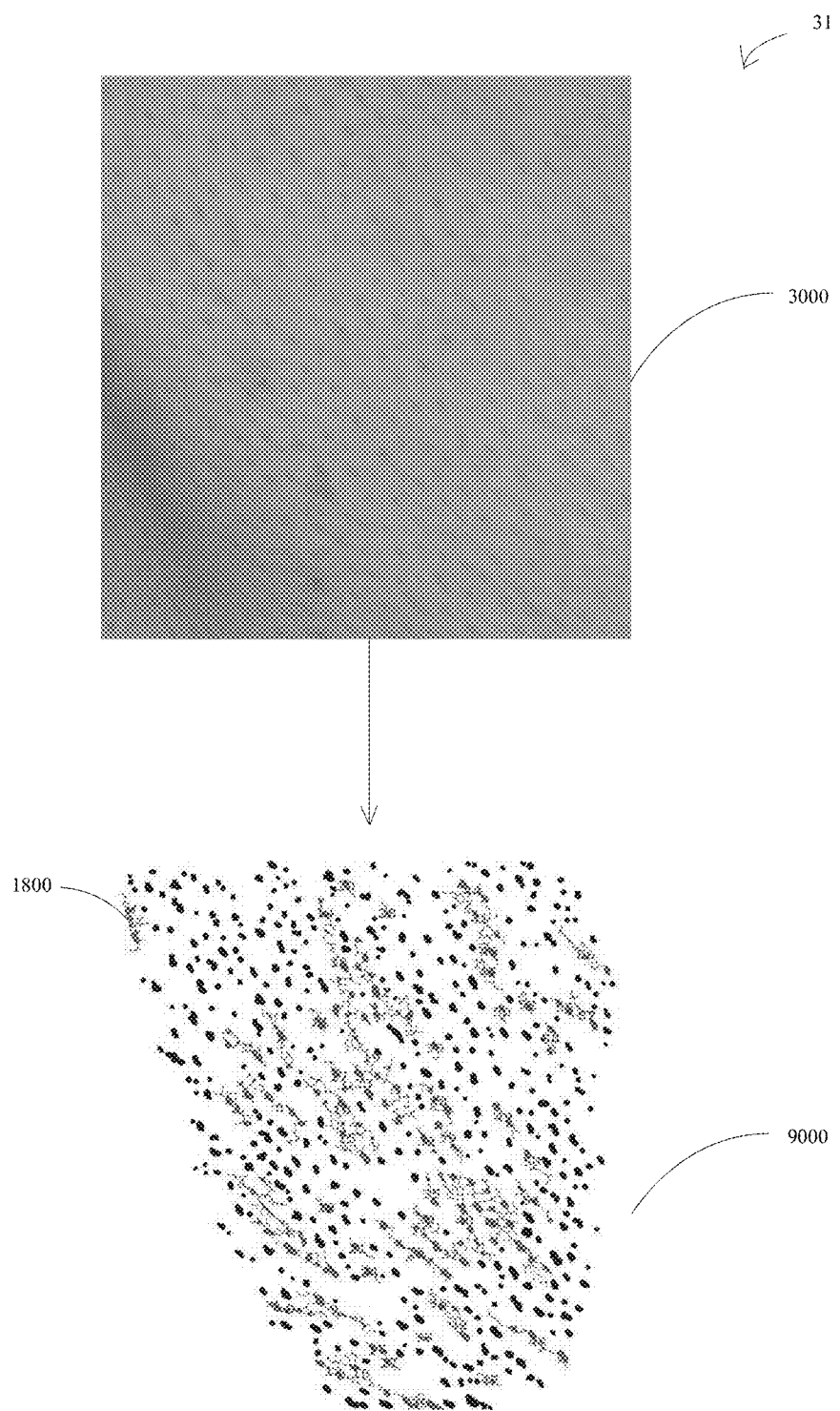
FIG. 3 is an image of a cheek, and a corresponding output of the method depicted of FIGS. 1 and 2 applied to the check image to identify a plurality of dendritic pores including clusters of these dendritic pores connected to one another.

FIG. 3 depicts a method of identifying dendritic pore clusters (31). An image of a cheek of the facial area of a subject is provided (3000). Applying the methods described from FIGS. 1 and 2, a first overlaid image comprising a plurality of dendritic pores are identified (9000). One example a dendritic pore cluster (1800) is identified in the first overlaid image (9000). 57 different dendric clusters are numbered in the first overlaid image (1800) of FIG. 3. These identified dendritic pores can be classified into one or more predetermined classes. Such classes may include: dendritic pore with one line; dendritic pore with two lines; dendritic pore with at least three lines; dendric pore connected to another dendric pore via at least one line; and combinations thereof.

Figure 4:
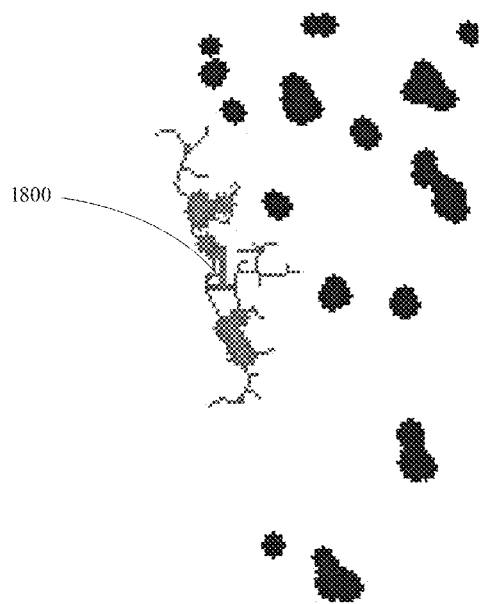
FIG. 4 is a close-up of one of the dendritic pore clusters of FIG. 3.

FIG. 4 is a close-up of a dendritic pore cluster (1800) of FIG. 3. The cluster is made up of six different dendritic pores. These pores of this cluster are connected by at least one line.

The methods herein may provide an additional displaying step. That is, identified dendritic pores or dendritic pore clusters, can be displayed to the subject. The display can be made by via a variety well known ways including websites or apps viewable through a computer. Preferably the display is be way of a mobile smart phone having a viewable screen.

The methods herein may also provide an addition step of determining a numerical severity associated, at least in part, with the identified dendritic pores for the subject (and displaying the determined numerical severity to the subject). A non-limiting example of such a numerical severity is one based on a scale from 1-5. 1 represents a minimal number of dendritic pores in a defined unit of facial area whereas 5 is a larger number of dendritic pores. Alternatively, the numerical severity may be associated with other skin parameters to provide a broader holistic numerical severity of the subject. Without limitation, these other skin parameters may include those based, at least on in part, on spots, texture, wrinkles, independent pores, skin tone, radiance and other imaging measurements. Yet other skin parameters may include those based on in vivo physical measurements such as dryness, hydration, barrier function, hydration, and sebum secretion.

The methods herein may provide yet still an addition step of generating a comparison between the subject's numerical severity and a predetermined value associated with a population of people. The population data used may be specific to the subject's age, geographic location, ethnic origin, or any other factor. See U.S. Pat. No. 6,571,003 B1, col. 9, lines 5-47, incorporated herein by reference.

EXAMPLE 1

Figure 5:
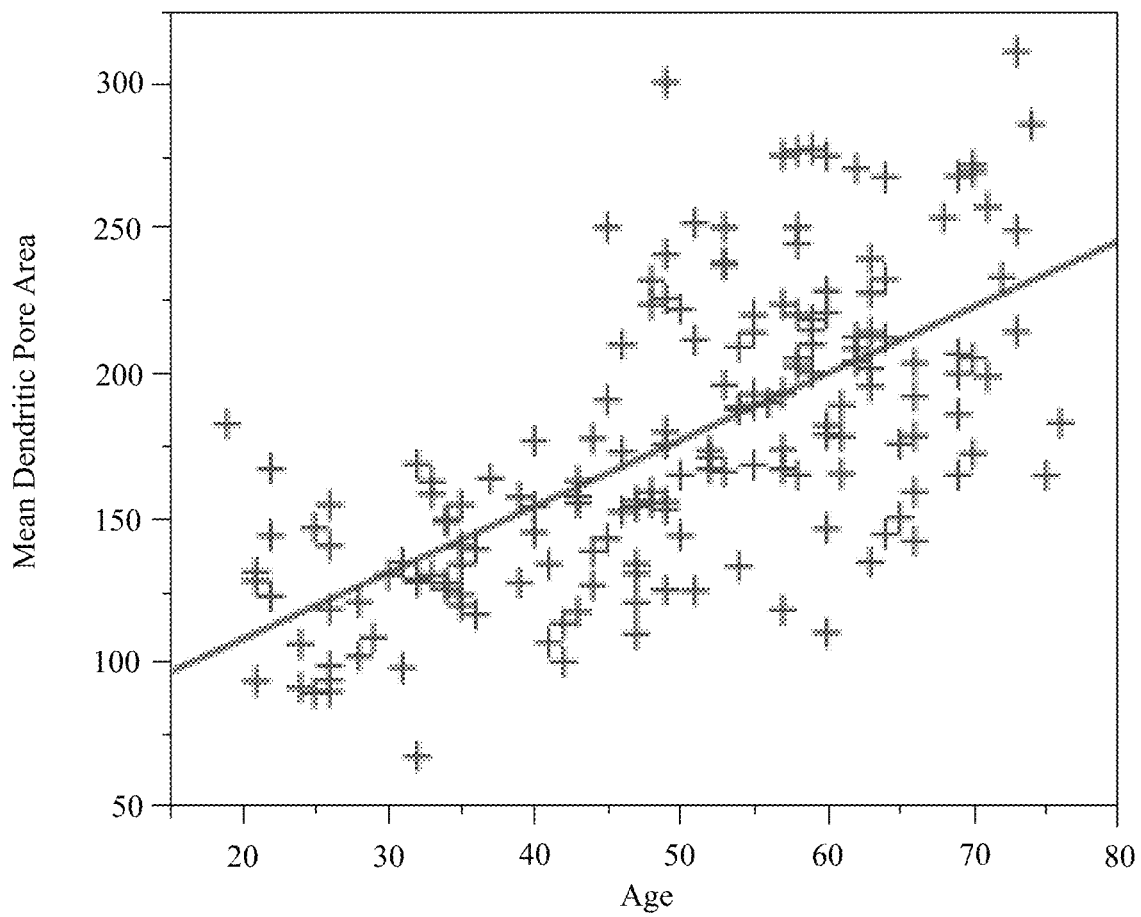
FIG. 5 is a graphic measuring the mean dendritic pore area of users from 20 to less than 80 years of age.

FIG. 5 is a table that plots the mean dendritic pore area as measured across users of different ages. These users ranged in chronological age from 20 to less than 80 years. Linear regression determines that the dendritic pore area increased annually at 2.14 arbitrary units. Digital images of a subjects' facial area skin are obtained by using the main camera of an iPhone® 7. Using the methods described above, the data of Table 1 is generated.

TABLE 1

Identifies the dendritic pore area across first and second user demographics, and dendritic pore area changes throughout the day in the second user demographic.

| Variable | Value |
| --- | --- |
| Mean dendritic pore area of first user demographic (20-35 years) | 199.87 arbitrary units |
| Mean age of first user demographic (n = 20 users) | 30.47 years |
| Mean dendritic pore area of second user demographic (>35 years) | 229.20 arbitrary units |
| Mean age of second user demographic (n = 24 users) | 44.18 years |
| Dendritic pore area increase per year, as determined by linear regression | 2.14 arbitrary units |
| Mean pore size change throughout day (morning vs. evening) in first user demographic | 19.39 arbitrary units |
| Mean pore size change equivalent to years in first user demographic (19.39/2.14) | 9.07 years equivalent |

A surprising finding is in the large increase in dendritic pore area that happens throughout the day, at least in the first user demographic. Specifically, when measured between the morning and evening of the same day, there is a mean change of over 19.39 arbitrary units. Dividing 19.39 by 2.14, i.e., the dendritic pore area increase on annual basis as (determined by linear regression across all users), represents a change of 9.07 years equivalent. This is dramatic increase in the "skin age" that happens throughout the day for at least the first user demographic. Accordingly, this provides an opportunity to develop non-medical skin care product and treatment regimens to address this daily change (in at least the first user demographic). Accordingly, one aspect of the invention provides using these methods of identifying dendritic pores in a subject in a frequency of more than once daily to track these changes to dendritic pores and/or the area of the dendric pores. For example, the methods of identifying dendritic pores herein are applied to a subject from 2-10 times daily to understand these changes and how a product or treatment may effect these changes. Preferably the methods are spaced at least 30 minutes apart, preferably at least one hour apart, more preferably at least once in the morning and once in the evening. The methods can also measure the area of the identified dendritic pore (so any changes in the area of identified dendritic pores can be assessed).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All numeric ranges described herein are inclusive of narrower ranges; delineated upper and lower range limits are interchangeable to create further ranges not explicitly delineated. Embodiments described herein can comprise, consist essentially of, or consist of, the essential components as well as optional pieces described herein. As used in the description and the appended claims, the singular forms "a," "an," and "the" are intended to include the plural forms as well, unless the context clearly indicates otherwise.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of identifying dendritic pores as a phenotype of skin aging, comprising:
    (a) obtaining a digital image of a subject's skin;
    (b) generating a line image having lines from the obtained digital image;
    (c) generating a pore image having pores from the obtained digital image;
    (d) overlaying the line image and the pore image to provide a first overlay image;
    (e) applying morphological reconstruction to the first overlay image to identify dendritic pores,
        i) wherein the pore image identifies boundaries of skin pores and the step of overlaying the line image and the pore image identifies those pores having at least one line intersecting the identified skin pore boundary to identify said dendritic pores and
        ii) the line image identifies boundaries of line and the step of overlaying the line image and the pore image identifies those pores having a least one line boundary intersecting the identified skin pore boundary to identify said dendritic pores; and
    (f) recommending a skin care treatment based on the dendritic pores.

2. The method of claim 1, further comprising the step generating a binary line image or a binary pore image, both a binary line image and a binary pore image.

3. The method of claim 1, further comprising the step of applying a shape filter to the obtained digital image of the subject's skin before generating the line image and the pore image.

4. The method of claim 3, wherein the shape filter comprises defining the pore by pore geometry parameters; wherein the pore geometry parameters are pore area, 25,000-1×10$^6$ micron$^2$, diameter, 175-1100 microns, width/length aspect ratio, 0.3-1, and combination thereof.

5. The method of claim 3, wherein the shape filter comprises defining the lines by line geometry parameters; wherein the line geometry parameters are selected from line thickness, wherein the line thickness is greater than 35 microns, line length, greater than 200 microns, and combination thereof.

6. The method of claim 1, wherein the step of obtaining a digital image of a subject's skin further comprises a step of performing histogram equalization to obtain a histogram-equalized image.

7. The method of claim 1, further comprises a step of filtering any one of the aforementioned images by removing one or more non-relevant skin features; said non-relevant skin features are selected from spot, hair, mole, pimple, acne, blackhead, and whitehead, and combinations thereof.

8. The method of claim 7, wherein the step of filtering comprises using at least a frequency filter, wherein the frequency filter is selected from the group: a Fast Fourier Transformation filter and Band Pass filter, a Difference of Gaussian filter, and any combinations thereof, the frequency filter is the Difference of Gaussian filter.

9. The method of claim 1, further comprising classifying the at least one dendritic pore into a predetermined class.

10. The method of claim 1, further comprising the step of displaying the identified dendritic pores to the subject, the displaying is via a smart phone.

11. The method of claim 1, further comprising the step of determining a numerical severity associated with the identified dendritic pores.

12. The method of claim 11, further comprising the step of generating a comparison between the subject's numerical severity and a predetermined value associated with a population of people.

13. The method of claim 1, further comprising the step of identifying dendritic pores in a subject on a frequency of more than once per day, 2-10 per day, the frequency spaced at least 1 hour apart; and comprising the additional step of determining the area of the identified dendritic pores.

14. The method of claim 9, wherein the predetermined class is selected from: dendritic pore with one line; dendritic pore with two lines; dendritic pore with at least three lines; dendric pore connected to another dendric pore via at least one line; and combinations thereof.

* * * * *